US010492816B2

(12) United States Patent
Loreth

(10) Patent No.: US 10,492,816 B2
(45) Date of Patent: Dec. 3, 2019

(54) LOAD SENSING RESECTION DEVICE

(71) Applicant: Smith & Nephew, Inc., Memphis, TN (US)

(72) Inventor: Brian Loreth, Braintree, MA (US)

(73) Assignee: Smith & Nephew, Inc., Memphis, TN (US)

(*) Notice: Subject to any disclaimer, the term of this patent is extended or adjusted under 35 U.S.C. 154(b) by 175 days.

(21) Appl. No.: 15/502,344

(22) PCT Filed: Aug. 6, 2015

(86) PCT No.: PCT/US2015/043994
§ 371 (c)(1),
(2) Date: Feb. 7, 2017

(87) PCT Pub. No.: WO2016/022790
PCT Pub. Date: Feb. 11, 2016

(65) Prior Publication Data
US 2017/0224370 A1    Aug. 10, 2017

Related U.S. Application Data

(60) Provisional application No. 62/034,991, filed on Aug. 8, 2014.

(51) Int. Cl.
*A61B 17/00*    (2006.01)
*A61B 17/32*    (2006.01)
(Continued)

(52) U.S. Cl.
CPC ........ *A61B 17/32002* (2013.01); *A61B 90/03* (2016.02); *A61B 90/98* (2016.02);
(Continued)

(58) Field of Classification Search
CPC .... A61B 17/32002; A61B 2017/00119; A61B 2017/00398; A61B 2017/00473; A61B 2017/00477; A61B 2017/00725
See application file for complete search history.

(56) References Cited

U.S. PATENT DOCUMENTS 5,192,292 A * 3/1993 Cezana ............ A61B 17/32002
604/22
2003/0125717 A1    7/2003 Whitman
(Continued)

FOREIGN PATENT DOCUMENTS

| EP | 2471617 A1 | 7/2012 |
| WO | 03047450 A2 | 6/2003 |
| WO | 2013009252 A2 | 1/2013 |

OTHER PUBLICATIONS

EP Examination Report dated Feb. 20, 2018 for corresponding European Patent Application No. 15754324.0-1113; 8 pages.
(Continued)

*Primary Examiner* — Katrina M Stransky

(57) ABSTRACT

Embodiments of the invention include drive units and other effective types of movement inducing devices that include load sensing mechanisms capable of giving feedback to a user when a force is being applied to the devices during use. The applied force for which monitoring is provided may be one or more of a lateral force transverse to a longitudinal rotating axis of a surgical blade, burr, or other mechanism, a force applied along the longitudinal rotating axis, and other forces.

11 Claims, 13 Drawing Sheets

(51) Int. Cl.
*A61B 90/00* (2016.01)
*A61B 90/98* (2016.01)
(52) U.S. Cl.
CPC ............. *A61B 2017/00119* (2013.01); *A61B 2017/00398* (2013.01); *A61B 2017/00473* (2013.01); *A61B 2017/00477* (2013.01); *A61B 2017/00725* (2013.01); *A61B 2090/064* (2016.02); *A61B 2217/005* (2013.01)

(56) References Cited

U.S. PATENT DOCUMENTS

| | | | | |
|---|---|---|---|---|
| 2008/0226409 | A1* | 9/2008 | Hasenzahl | A61C 1/00 409/231 |
| 2010/0262145 | A1* | 10/2010 | Kaji | A61B 17/1622 606/79 |
| 2010/0324541 | A1 | 12/2010 | Whitman | |
| 2012/0143203 | A1* | 6/2012 | Nishio | A61B 17/1631 606/96 |
| 2013/0018400 | A1* | 1/2013 | Milton | A61B 17/32002 606/167 |

OTHER PUBLICATIONS

Search Report and Written Opinion of PCT/US2015/043994 dated Sep. 30, 2015.
EP Examination Report dated Apr. 15, 2019 for corresponding European Patent Application No. 15754324.0-1113; 6 pages.

\* cited by examiner

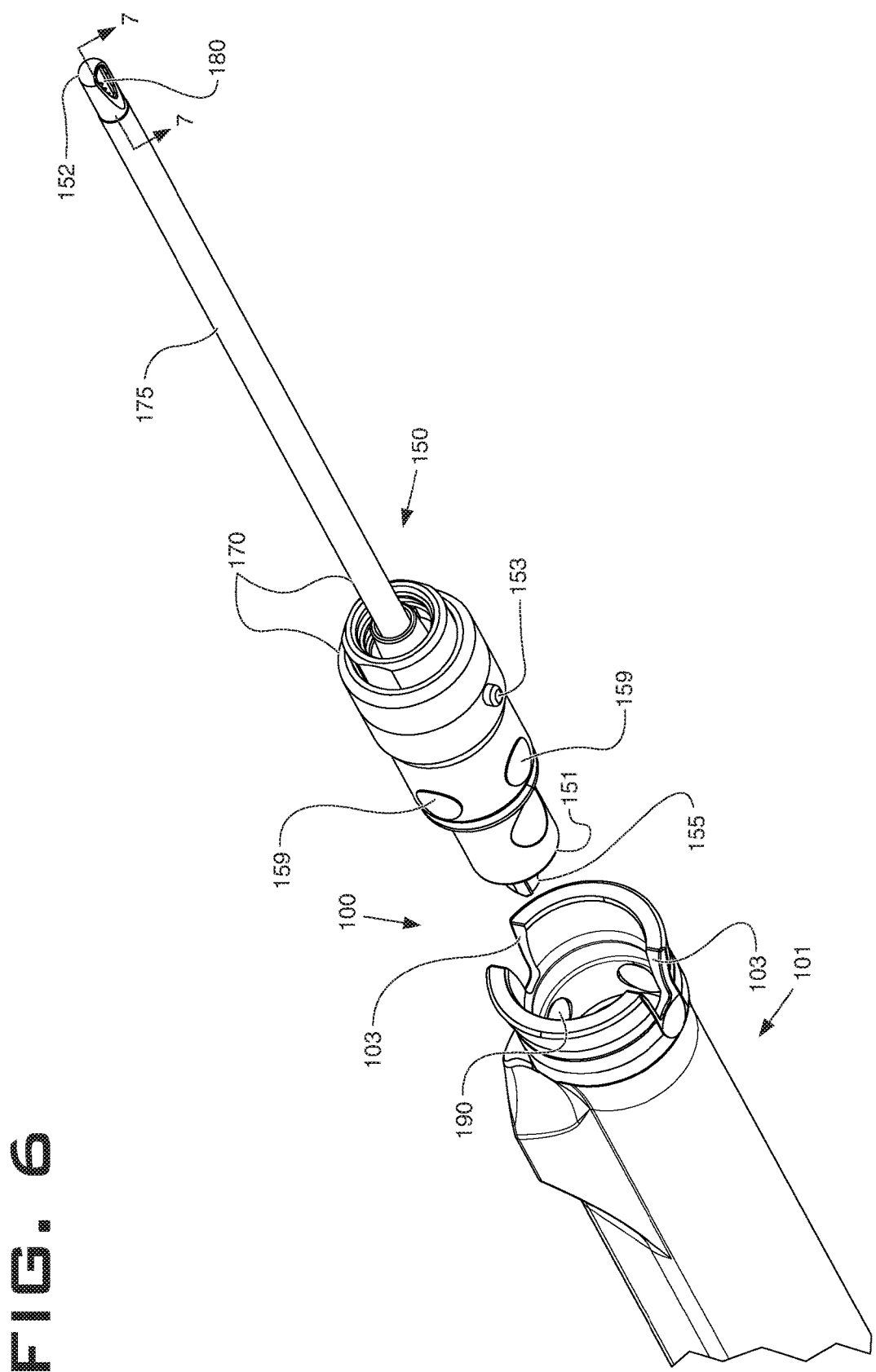

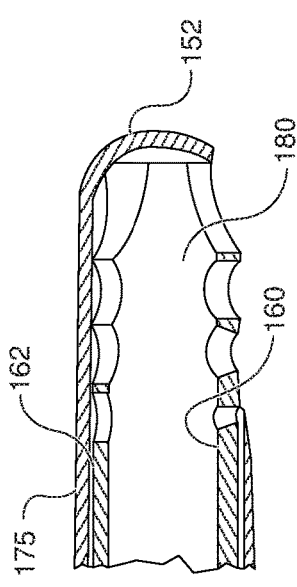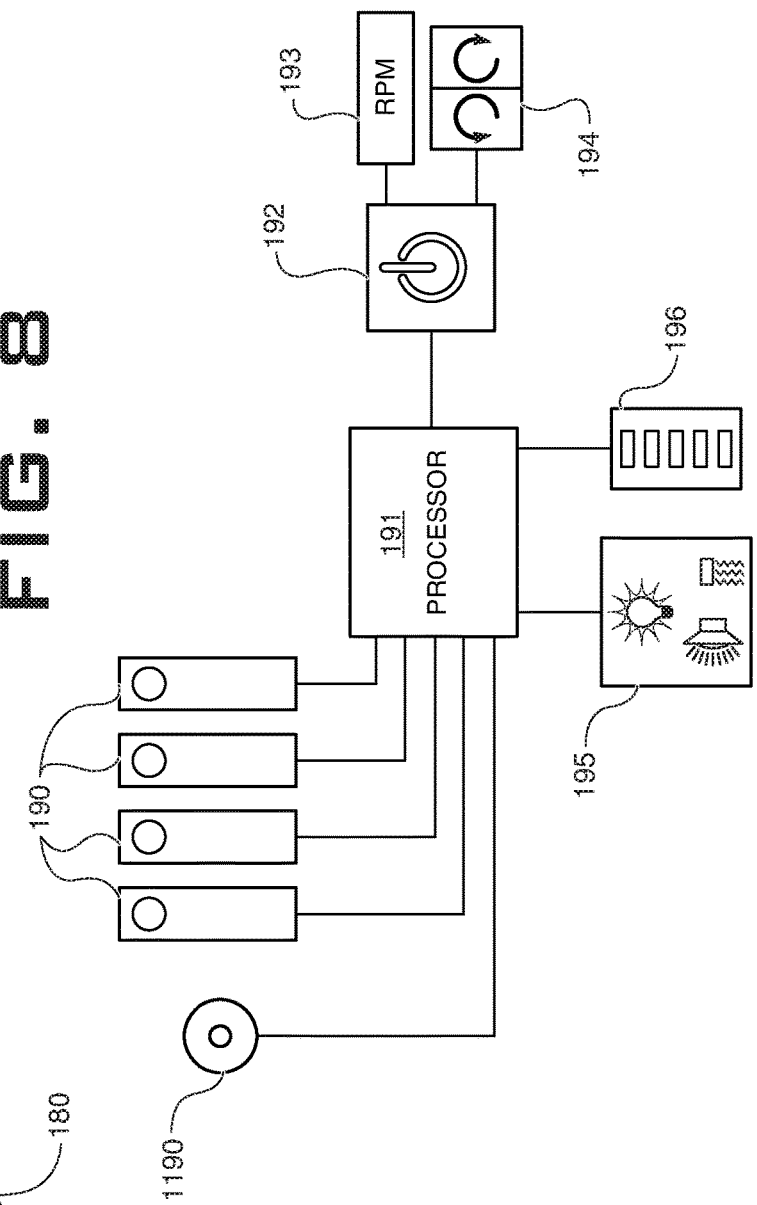

LOAD SENSING RESECTION DEVICE

CROSS-REFERENCE TO RELATED APPLICATIONS

This application is a U.S. National phase entry of PCT/US2015/043994 filed Aug. 6, 2015 and titled "Load Sensing Resection Device." PCT/US2015/043994 claims the benefit of U.S. Prov. Pat. Appl. Ser. No. 62/034,991 filed Aug. 8, 2014. Both applications are incorporated by reference herein as if reproduced in full below.

FIELD OF INVENTION

The various embodiments relate to the field of surgical instruments, and more particularly relates to surgical instruments for resecting, cutting, or otherwise manipulating tissue and related methods. Some embodiments include mechanisms capable of sensing loads applied to surgical instruments during use.

BACKGROUND

Surgical cutting or resection devices with drive units and rotating blades or burrs are commonplace in endoscopic surgery. Many current devices include a reusable drive unit and disposable rotating blades, burrs, or other attachments that are configured to couple to the reusable drive unit. During an endoscopic surgery, a surgeon may unknowingly apply forces to an instrument that have the potential of damaging the instrument or causing complications to the surgical procedure when using instruments of the previously existing designs.

It would be advantageous to provide surgical instruments for endoscopic surgery that are capable of monitoring forces applied to the instruments. It may be further advantageous to have the capability to provide alerts of one or more types that notify a user when load limits that have been set for forces applied to the instruments have been reached. Some improved embodiments may include methods of calibrating a cutting tool with integrated force sensors to provide an alert when load limits are reached and methods of calculating loads applied to a cutting tool.

SUMMARY

An embodiment of the invention is a cutting tool that includes a drive unit, a working assembly having a proximal end, a distal end, and a longitudinal axis that passes between the proximal end and the distal end, the working assembly configured to couple with and at least in part be rotated by the drive unit, and two or more sensors positioned between the drive unit and the working assembly. The two or more sensors may be positioned to detect force applied to the working assembly transverse to the longitudinal axis of the working assembly while the working assembly is coupled to the drive unit.

Another embodiment of the invention is a cutting tool that includes a drive unit, a rotatable shaft mounted in a housing and configured to be coupled with the drive unit at a proximal end of the rotatable shaft and be rotated by the drive unit, a cutting element at a distal end of the rotatable shaft, and a plurality of force sensors. The force sensors may be spaced around the housing of the rotatable shaft such that forces applied to the cutting element, rotatable shaft, or housing transverse to an axis of rotation of the rotatable shaft from any transverse direction are measurable as forces applied to one or more of the force sensors.

Yet another embodiment of the invention is a method of calibrating a cutting tool with integrated force sensors. The method may include providing a drive unit, providing a working assembly having a proximal end, a distal end, and a longitudinal axis that passes between the proximal end and the distal end, the working assembly configured to couple with and at least in part be rotated by the drive unit, and providing sensors configured to measure loads applied to the working assembly. The method may also include the acts of applying a limit load to the working assembly, registering a measured load on one or more of the sensors that results from application of the limit load, and setting an alert to be activated when the measured load registered on one or more sensors is reached.

Still another embodiment of the invention is a method of determining a lateral load on a cutting tool with one or more rotating components. The method may include providing a drive unit, providing a working assembly having a proximal end, a distal end, and a longitudinal axis that passes between the proximal end and the distal end, the working assembly including a shaft configured to at least in part be rotated by the drive unit, and providing two or more sensors positioned between the drive unit and the working assembly at intervals around the longitudinal axis of the working assembly. The method may also include the acts of operating the cutting tool and applying a lateral load to the cutting tool and measuring loads at the two or more sensors while the cutting tool is being operated. If only one sensor measures a significant load while the tool is being operated, then the method may include comparing the measured load to a limit load to determine if an alert should be activated. If more than one sensor measures a significant load while the tool is being operated, then the method may include calculating a resultant load from the loads measured and comparing the resultant load to the limit load to determine if an alert should be activated.

BRIEF DESCRIPTION OF THE DRAWINGS

FIG. 6 is a perspective view of a portion of the cutting tool of FIG. 1.

FIG. 7 is a cross-sectional view of a distal end of the cutting tool of FIG. 1 taken through the section illustrated in FIG. 6.

FIG. 8 is a system diagram of an embodiment of a drive unit, sensors, and related equipment.

DETAILED DESCRIPTION

A cutting tool 100 and its component parts are illustrated in FIGS. 1-7. As used herein the term "cutting tool" may include not only tools that cut with a blade but tools that abrade, scratch, rub, dislodge, or otherwise manipulate tissue. The cutting tool 100 illustrated includes a drive unit 101 and a working assembly 150. The drive unit 101 may be a motorized drive unit powered by an electric motor and a battery, transformer, capacitor, wire, or other source of electricity, may be powered by air pressure or other fluid pressure, may be powered by manual or automated user manipulation, or may be powered by any other effective mechanism. A set of controls 105 is illustrated in FIGS. 1, 2, 4, and 5. The set of controls 105 may include buttons, switches, sliders, indicators, and other mechanisms or displays to adjust and control functions of the drive unit 101. For example and without limitation, the controls 105 may be used to one or more of power the drive unit 101 on and off, set a rotating speed for a portion of the drive unit, activate a clockwise or counterclockwise rotation of a portion of the drive unit, indicate a status or function of the drive unit 101, set or express an alert function associated with the cutting tool 100 or any of its component parts, and provide any other useful control or display associated with the drive unit 101. Function and control of the drive unit 101 in combination with the other components of the cutting tool 100 will be described in greater detail in association with FIG. 8 below. Function and control may also be accomplished by use of a control system coupled with the drive unit 101, and may further include use of separate controls such as foot operated controls.

Figure 1:
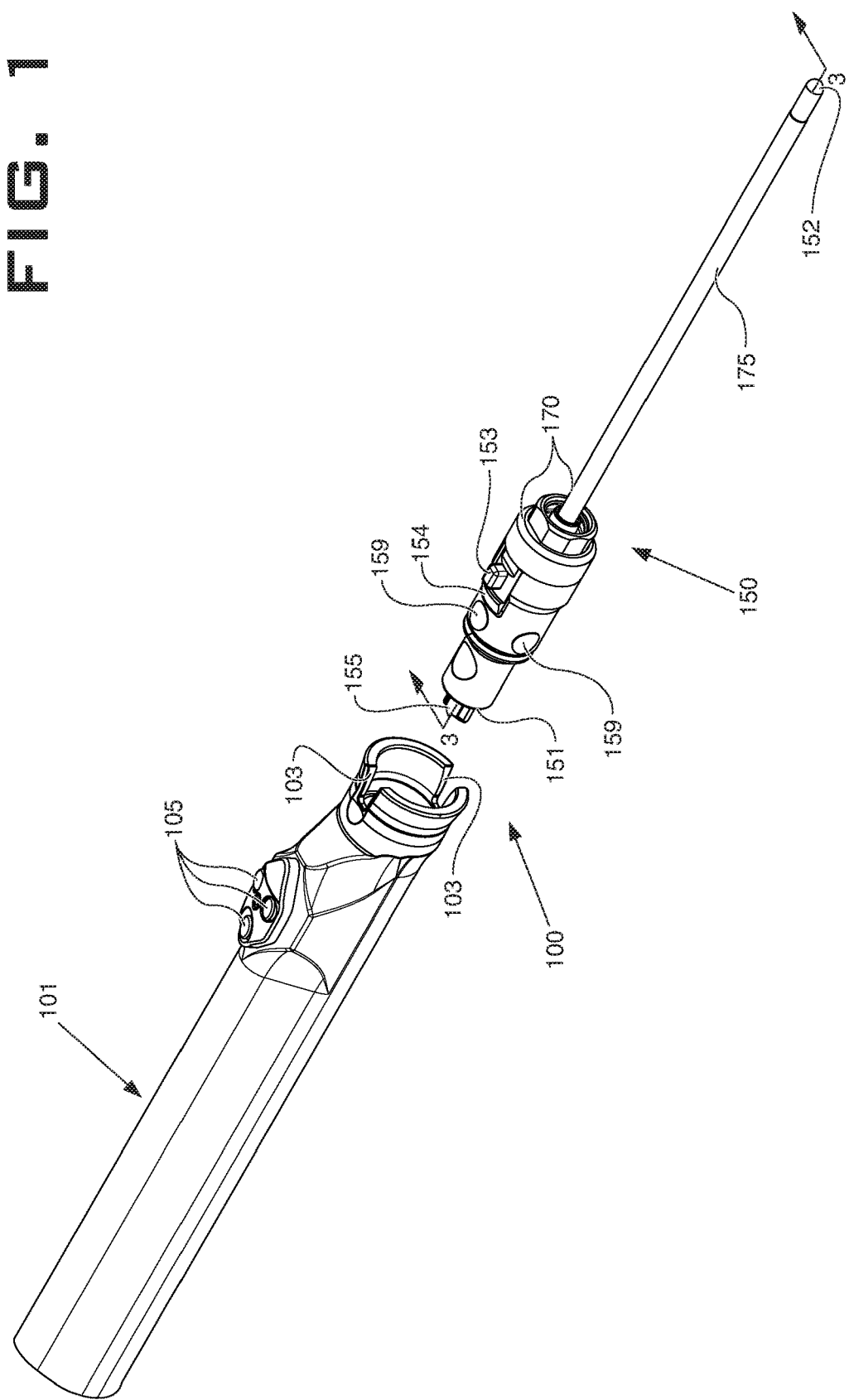
FIG. 1 is a partially exploded perspective view of an embodiment of a cutting tool.
Figure 2:
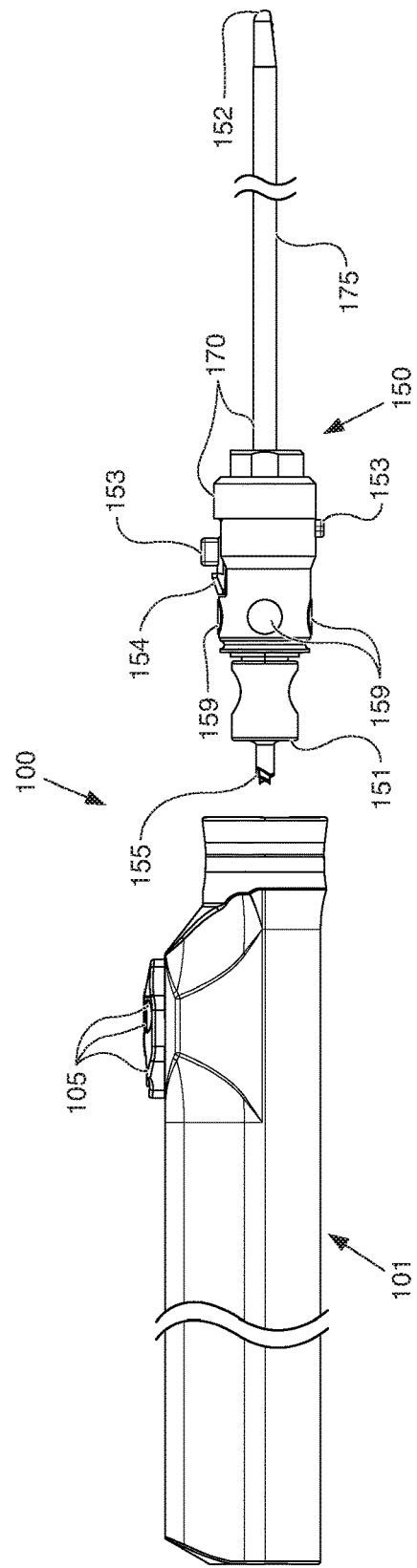
FIG. 2 is a side elevation view of the cutting tool of FIG. 1.
Figure 3:
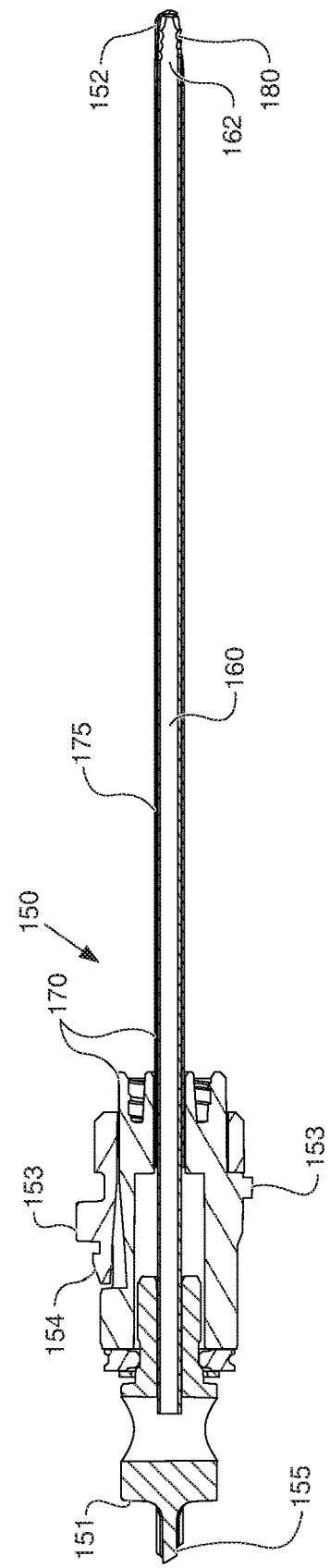
FIG. 3 is a cross-sectional view of a portion of the cutting tool of FIG. 1.
Figure 4:
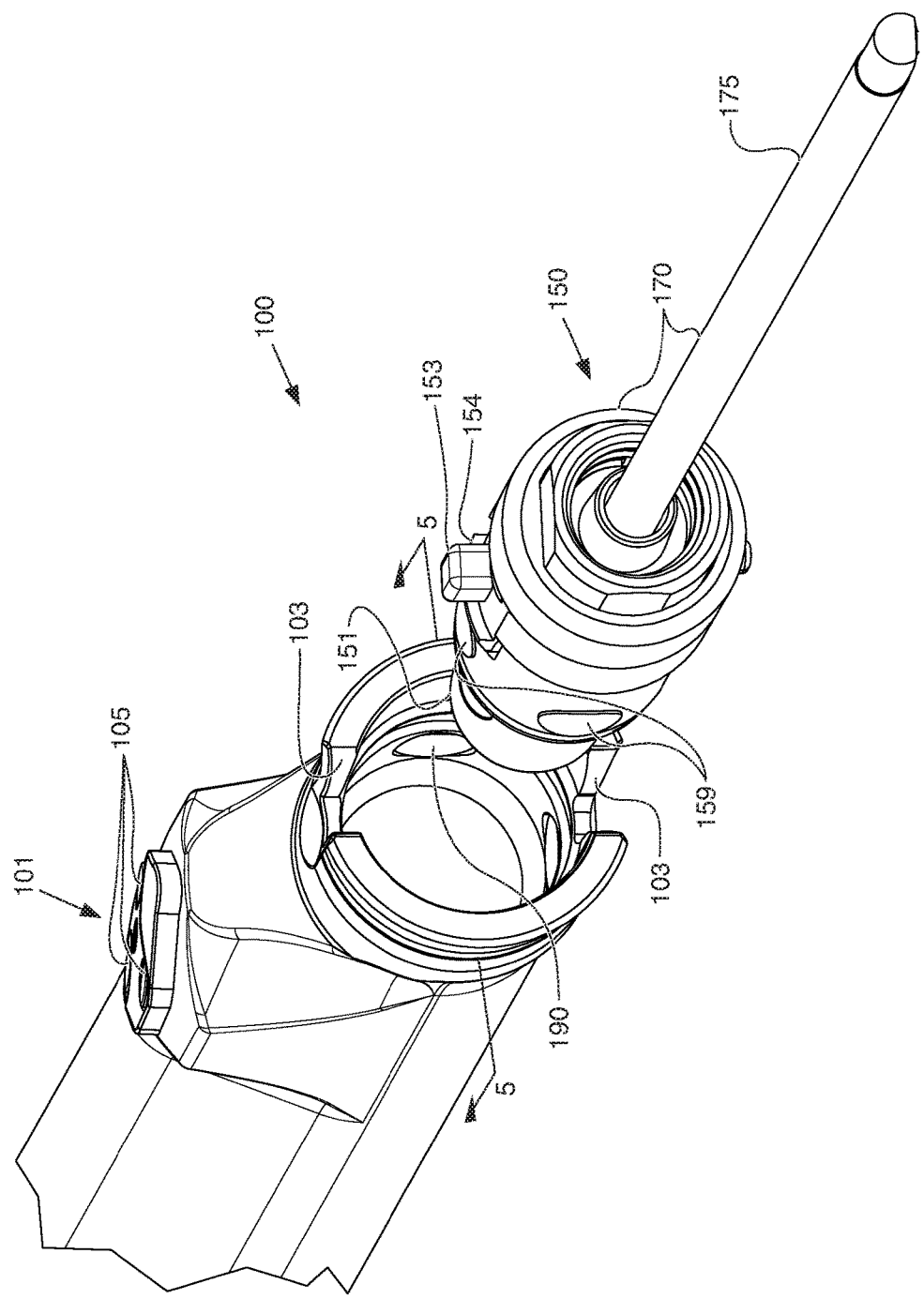
FIG. 4 is an additional perspective view of the cutting tool of FIG. 1.

The working assembly 150 illustrated in FIGS. 1-4, 6, and 7 includes a proximal end 151 a distal end 152 and the longitudinal axis that passes between the proximal end 151 and the distal end 152. The working assembly 150 shown is configured to couple with the drive unit 101 and at least in part be rotated by the drive unit 101. As is most clearly shown in FIG. 3, the working assembly 150 may include a housing 170. The housing 170 may include a cannular shaft 175 extending toward the distal end of the working assembly 150. A rotatable shaft 160 is shown mounted in the housing 170 and the rotatable shaft 160 in the illustrated embodiment is configured to be coupled with the drive unit 101 at the proximal end 151 of the working assembly 150 and the rotatable shaft 160. The working assembly 150 and the drive unit 101 are coupled by alignment of guide pins 153 (FIGS. 1-4 and 6) and notches 103 (FIGS. 1, 4 and 6). Releasable locking of the working assembly 150 with the drive unit 101 is accomplished with a latch 154. Insertion of the working assembly 150 into the drive unit 101 leads to engagement of the latch 154 with the drive unit 101. The latch 154 may be released by pressing the adjacent guide pin 153. While pressed, the working assembly 150 may be removed from the drive unit 101. The working assembly 150 includes a torque transfer element 155 (FIGS. 1-3 and 6) configured to engage with and be turned by the drive unit 101. The torque transfer element 155 is coupled with the rotatable shaft 160 (FIG. 3) to enable the rotatable shaft 160 to be turned by the drive unit 101. The working assembly 150 shown also includes seating pads 159, as shown in FIGS. 1, 2, 4, and 6, configured to make contact with sensors 190 when the working assembly 150 is coupled with the drive unit 101. The seating pads 159 shown are configured to ensure a consistent load transfer between the working assembly 150 and the drive unit 101. In other embodiments, devices such as the seating pads 159 may or may not be used to guide load transfer between a working assembly and a drive unit.

A cutting element 180 is shown in FIGS. 3, 6, and 7 coupled at a distal end 162 of the rotatable shaft 160. In other embodiments, a cutting element may be a module or component configured to couple at a distal end of the shaft by any effective mechanism. Cutting elements may also be integral with a rotatable shaft and may be formed from the same material as a rotatable shaft. Cutting elements of various embodiments may include blades, burrs, rasps, abrasives, or any other devices effective to cut, abrade, scratch, rub, dislodge, or otherwise manipulate tissue.

Figure 5:
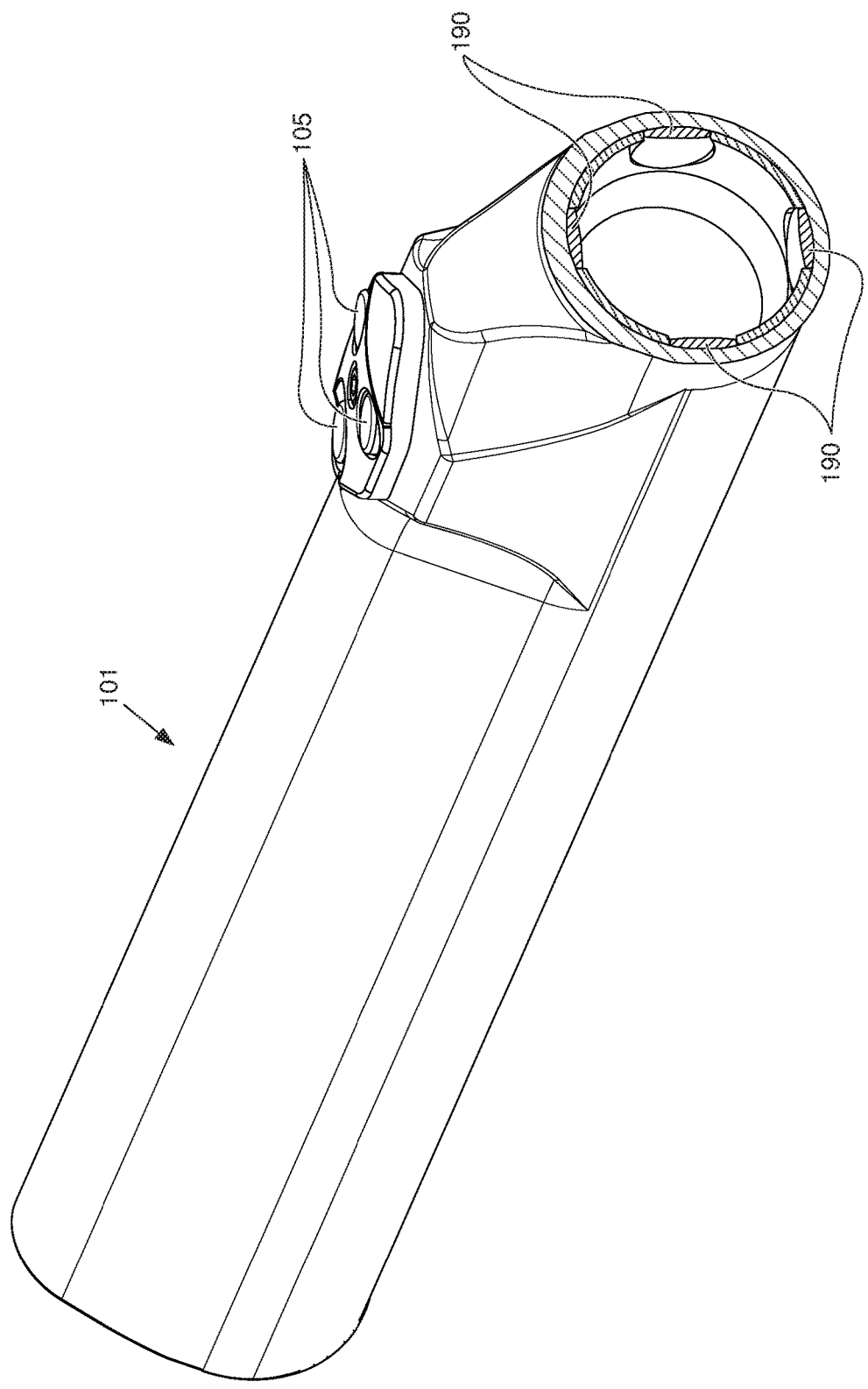
FIG. 5 is a cross-sectional perspective view of a portion of the cutting tool of FIG. 1 taken through the section illustrated in FIG. 4.

Sensors 190 are shown in FIGS. 4-6 configured to be positioned between the drive unit 101 and the working assembly 150. The sensors 190 depicted are force sensors configured to measure loads applied to the faces of the sensors. In the illustrated embodiment, as best seen in FIG. 5, there are four sensors 190 positioned substantially radially equidistantly around the longitudinal axis of the working assembly 150 when the working assembly 150 is coupled with the drive unit 101. In other embodiments, sensors may be positioned at other effective locations within a cutting tool. For example and without limitation, three sensors positioned substantially radially equidistantly around the longitudinal axis of a working assembly when the working assembly is coupled with the drive unit could be used. In the illustrated embodiment, the sensors 190 are integral with the drive unit 101. In other embodiments, similar sensors could be integral with a working assembly or could be separate components that are positioned between a drive unit and a working assembly without being integral with either. In the embodiment illustrated, the sensors 190 are spaced around the periphery of the housing 170 of the rotatable shaft 160 when the working assembly 150 is coupled with the drive unit 101. In this configuration, forces that are applied to the cutting element 180 within the housing 170 transverse to an axis of rotation of the rotatable shaft 160 from any transverse direction are measurable as forces applied to one or more of the sensors 190. The sensors 190 shown are positioned to detect force applied to the working assembly 150 transverse to the longitudinal axis of the working assembly 150 while the working assembly 150 is coupled to the drive unit 101. Load may further be applied to the working assembly 150 by application of force to any part of the housing 170, including the cannular shaft 175, and may be applied through the cutting element 180 and the rotatable shaft 160.

Sensors 190, 290 (FIGS. 9-12), 1190 (FIG. 14) may be any effective type of sensor for the applications described herein, including but not limited to, force sensors, pressure sensors, proximity sensors, movement sensors, and other types of tactile sensors. For example and without limitation, sensors may be thin film load cells, devices employing piezoelectric elements, variable capacitance detectors, and strain gauges. Piezoresistive material built on a flexible polyester circuit material with conductive traces may also be used as a sensor with some embodiments. Sensors of various embodiments may be discrete elements physically separate from one another or may include two or more sensors built onto a common structure or backing.

Function and control of the drive unit 101 in combination with the other components of the cutting tool 100 are illustrated in a system diagram in FIG. 8. Sensors 190 are shown electrically coupled with a processor 191. An axial sensor 1190 (FIG. 14) is also shown electrically coupled with the processor 191. The axial sensor 1190 may be present with any of the cutting tools 100, 200, 300 illustrated or with similar cutting tools within the scope of the present disclosure. The processor 191 is configured to not only receive and interpret signals from the sensors 190, 1190, but also to control and display the functions and status of the drive unit 101. The processor 191 is coupled with a power control 192, which is coupled with a revolution rate selector 193 and a revolution direction selector 194. The processor 191 is also coupled with an alert control 195 and an indicator 196. The alert control 195 may be used to one or both select and indicate whether an alert is to be provided with a lighted indication, an audible indication, a vibratory indication, or any other effective indication. The indicator 196 may be used in association with one or more of the other functions of the drive unit 101. For example and without limitation, the indicator 196 may be used to set or display a speed or direction of rotation for the device, may be used as a power indicator, may be used to indicate an acceptable limit load being set for the cutting tool 100, or may be used for one or a combination of these or other purposes. Control and display functions may be accomplished with hardwired or so-called "soft" function buttons or keys that are part of the drive unit 101, such as for example, the set of controls 105 illustrated. The system may further include display screens of various types. These and other function and control mechanisms may alternatively or in combination be performed by an external control system as more fully described in association with FIG. 13.

A cutting tool 200 and its component parts are illustrated in FIGS. 9-12. The cutting tool 200 illustrated includes a drive unit 201 and a working assembly 250. A set of controls 205 is illustrated in FIGS. 9-12. The set of controls 205 may be essentially similar to the controls 105 described herein. Function and control of the drive unit 201 in combination with the other components of the cutting tool 200 may be essentially similar to the descriptions provided herein for the drive unit 101 in association with FIG. 8.

Figure 9:
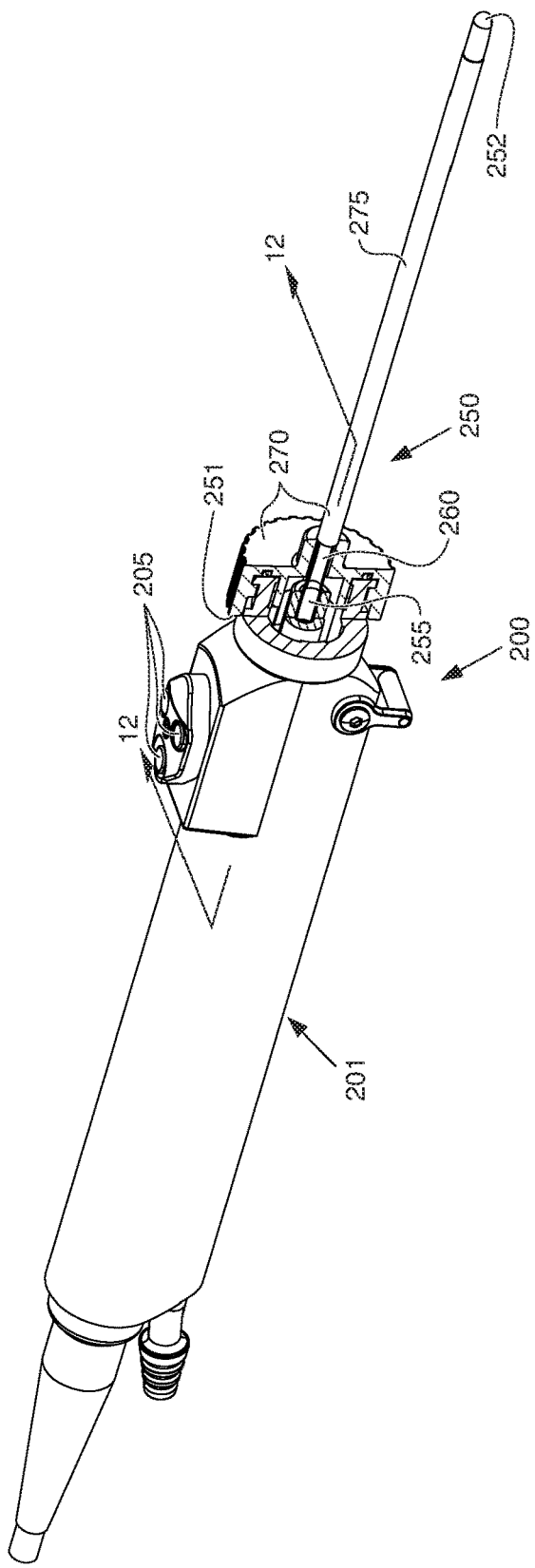
FIG. 9 is a perspective view of an embodiment of a cutting tool with a partial cut-away section provided to illustrate some internal operation and connectivity of the cutting tool.
Figure 10:
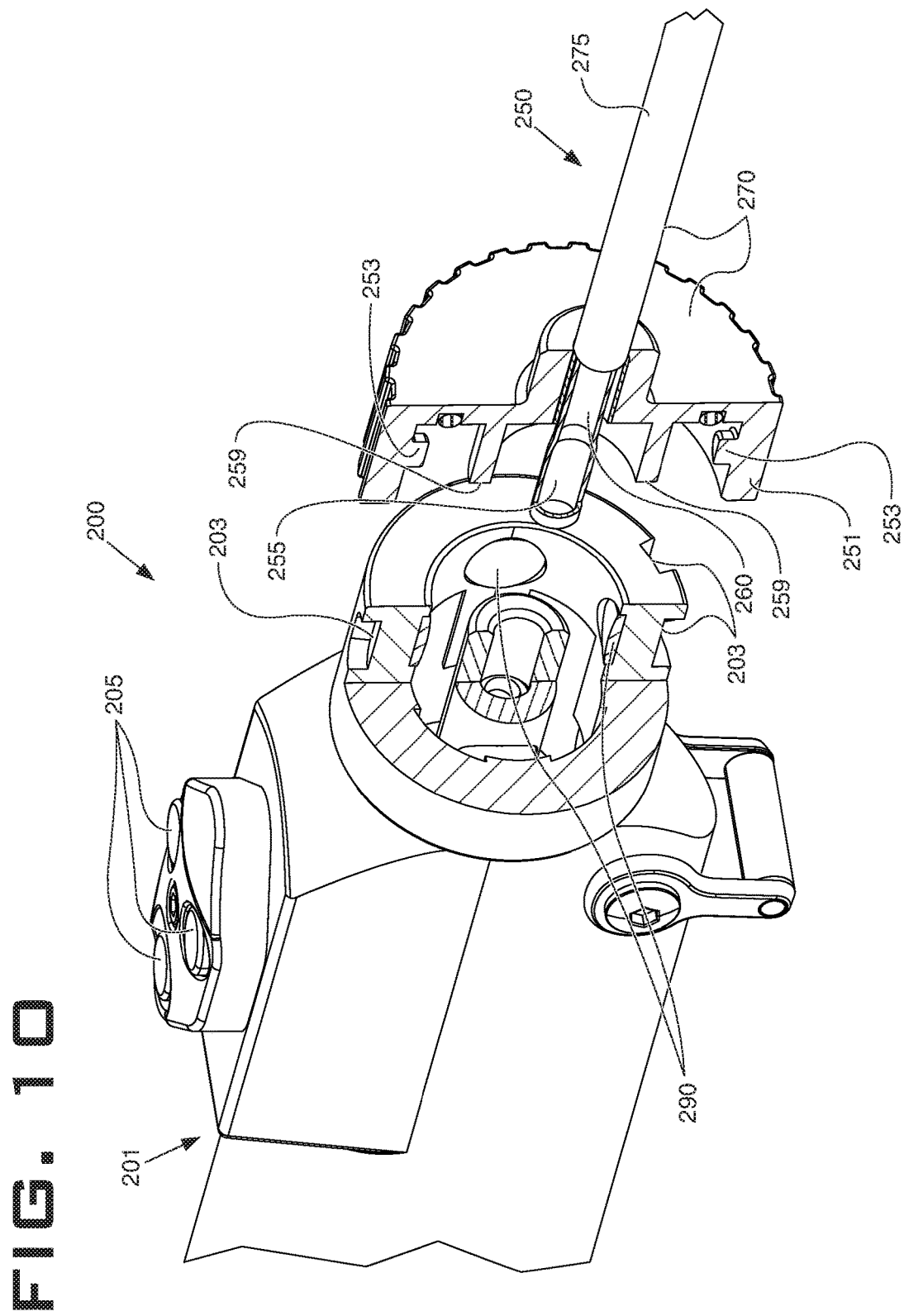
FIG. 10 is a partially exploded perspective view with a partial cut-away of the cutting tool of FIG. 9.
Figure 11:
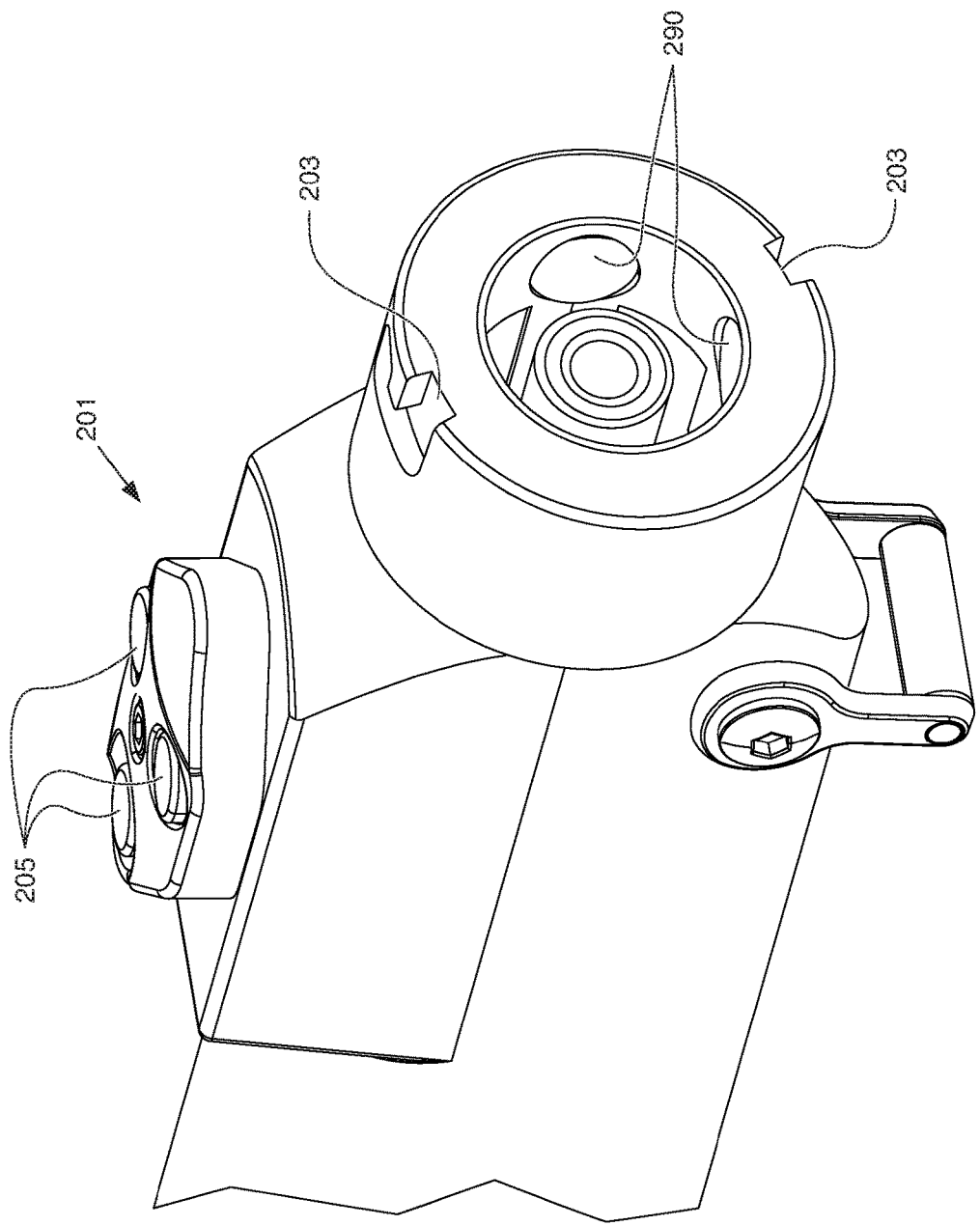
FIG. 11 is a perspective view of a drive unit of the cutting tool of FIG. 9.
Figure 12:
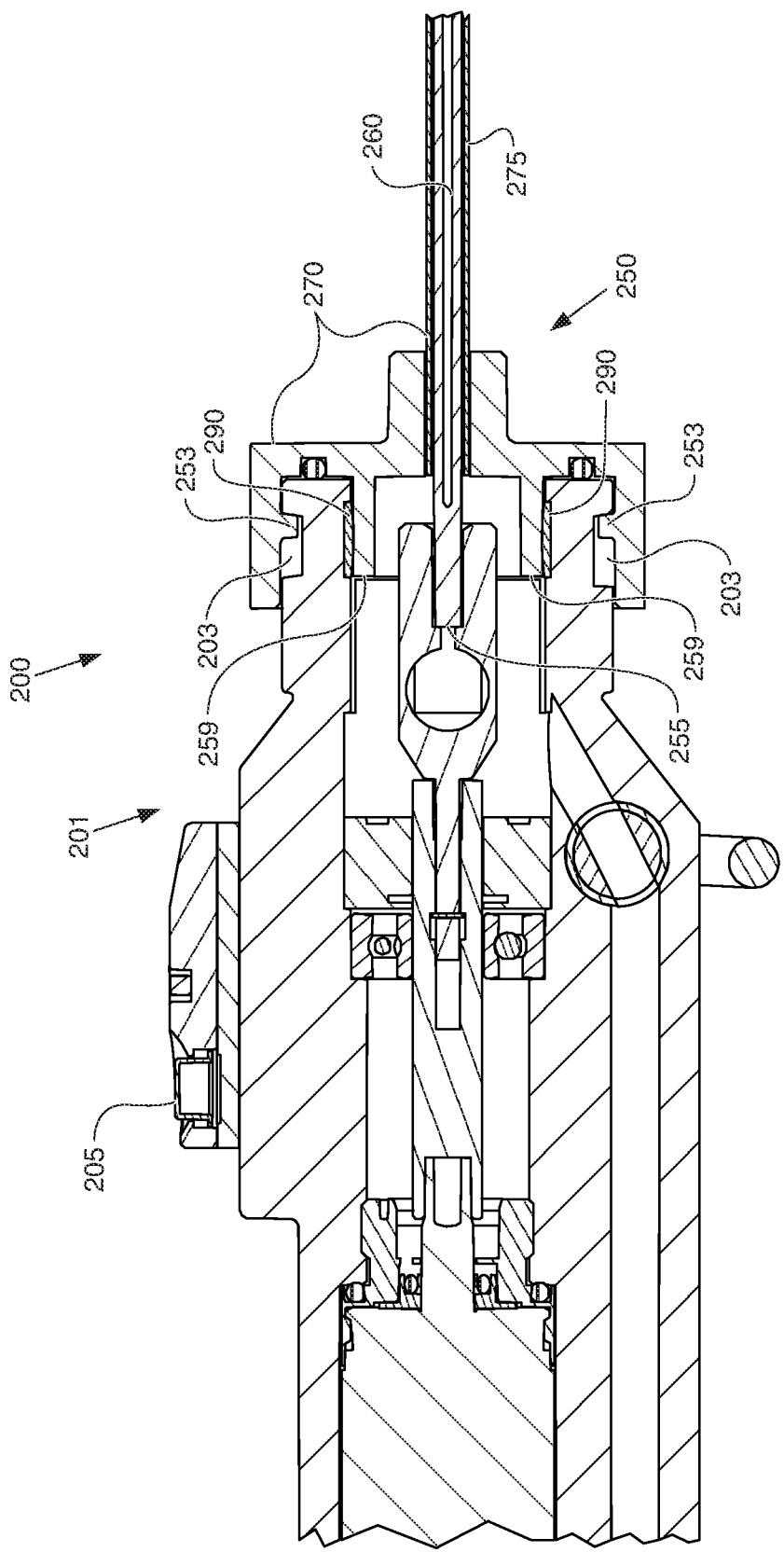
FIG. 12 is a cross-sectional view of a portion of the cutting tool of FIG. 9 taken through the section illustrated in FIG. 9.

The working assembly 250 illustrated in FIGS. 9, 10, and 12 includes a proximal end 251, a distal end 252, and a longitudinal axis that passes between the proximal end 251 and the distal end 252. The working assembly 250 shown is configured to couple with the drive unit 201 and at least in part be rotated by the drive unit 201. The working assembly 250 may include a housing 270. The housing 270 may include a cannular shaft 275 extending toward the distal end of the working assembly 250. A rotatable shaft 260 is shown mounted in the housing 270 and in the illustrated embodiment is configured to be coupled with the drive unit 201 at the proximal end 251 of the working assembly 250 and the rotatable shaft 260. The working assembly 250 and the drive unit 201 are coupled by alignment of guide pins 253 in notches 203 (FIGS. 10-12) and rotation of the working assembly 250 to move the guide pins 253 through paths of the notches 203. Releasable locking of the working assembly 250 with the drive unit 201 is accomplished by clockwise rotation while compressing, and unlocking is accomplished by counterclockwise rotation with an initial compression and then separation of the working assembly 250 from the drive unit 201. The working assembly 250 includes a torque transfer element 255 (FIGS. 9, 10, and 12) configured to engage with and be turned by the drive unit 201. The torque transfer element 255 is coupled with the rotatable shaft 260 (FIG. 12) to enable the rotatable shaft 260 and be turned by the drive unit 201. A cutting element essentially similar to the cutting element 180 may be coupled at a distal end of the rotatable shaft 260.

Sensors 290 are shown configured to be positioned between (FIGS. 10 and 11) and actually positioned between (FIG. 12) the drive unit 201 and the working assembly 250. The sensors 290 depicted are force sensors configured to measure loads applied to the faces of the sensors. In the illustrated embodiment, there are four sensors 290 positioned substantially radially equidistantly around the longitudinal axis of the working assembly 250 when the working assembly 250 is coupled with the drive unit 201. In other embodiments, sensors may be positioned at other effective locations within a cutting tool. For example and without limitation, three sensors positioned substantially radially equidistantly around the longitudinal axis of a working assembly when the working assembly is coupled with the drive unit could be used. In the illustrated embodiment, the sensors 290 are integral with the drive unit 201. In other embodiments, similar sensors could be integral with a working assembly or could be separate components that are positioned between a drive unit and a working assembly without being integral with either. In the embodiment illustrated, the sensors 290 are spaced around the periphery of a flange 259 of the housing 270 when the working assembly 250 is coupled with the drive unit 201. In this configuration, forces that are applied to the cutting element at the distal end of the rotatable shaft 260 within the housing 270 transverse to an axis of rotation of the rotatable shaft 260 from any transverse direction are measurable as forces applied to one or more of the sensors 290. The sensors 290 shown are positioned to detect force applied to the working assembly 250 transverse to the longitudinal axis of the working assembly 250 while the working assembly 250 is coupled to the drive unit 201. Load may further be applied to the working assembly 250 by application of force to any part of the housing 270 including the cannula shaft 275, and may be applied through the cutting element and the rotatable shaft 260. The sensors 290 may be any effective type of sensor for the applications described herein and may be essentially similar to the sensors 190, 1190 described above.

Function and control of the drive unit 201 in combination with the other components of the cutting tool 200 are essentially similar to the function and control illustrated in the system diagram in FIG. 8.

Figure 13:
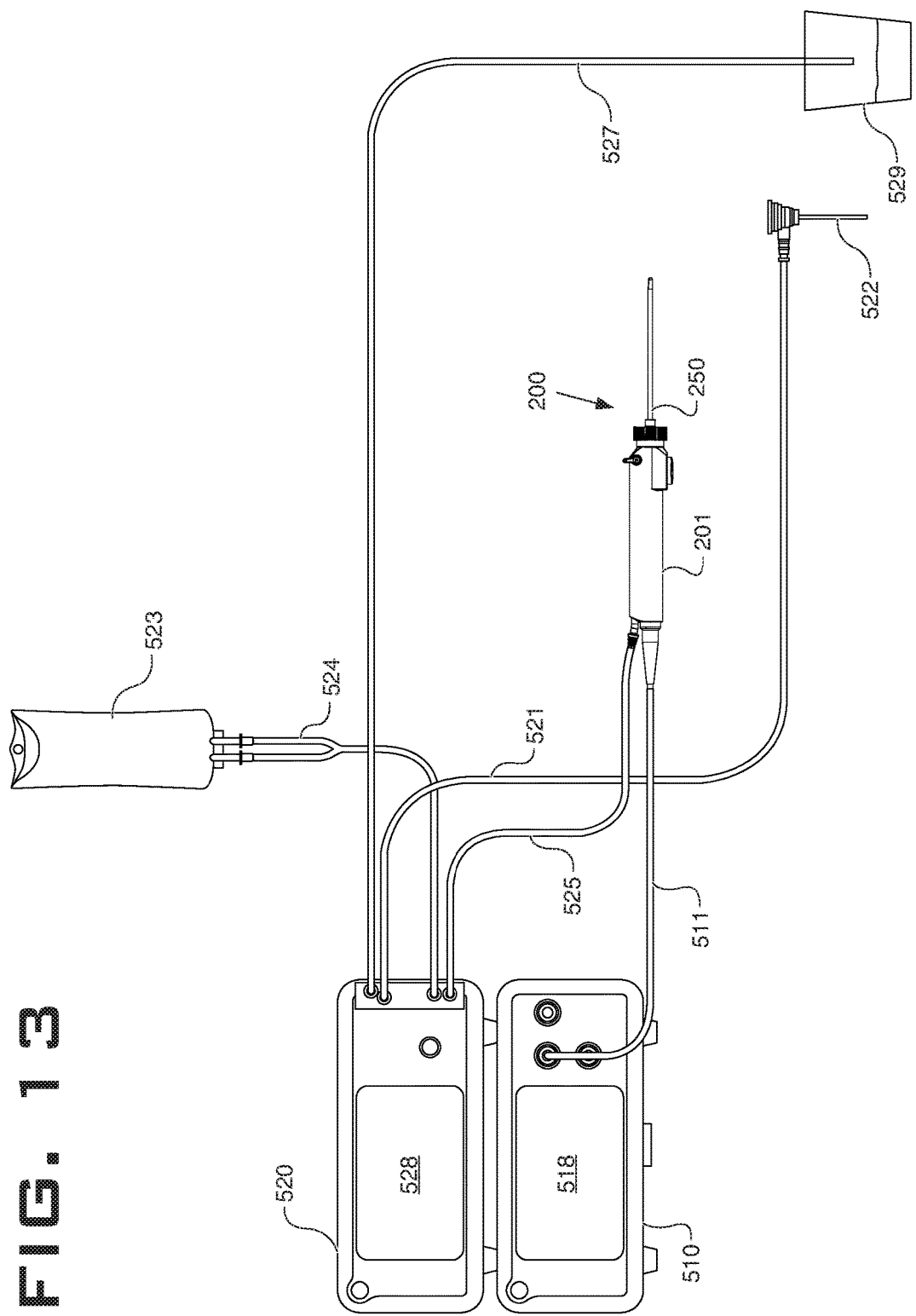
FIG. 13 is a system diagram of the cutting tool of FIG. 9 in combination with a control system for controlling use of the cutting tool and managing fluids.

A control system is illustrated in FIG. 13 coupled with the drive unit 201, which is couple with the working assembly 250, of the cutting tool 200. The same or an essentially similar control system may be used with the cutting tools 100, 300. The control system shown in FIG. 13 includes a resection control 510 that is electrically coupled with the drive unit 201 by a cable 511. The resection control 510 may be used to one or more of provide power to the drive unit 201, receive operator inputs from the drive unit 201, sense operating parameters of the drive unit 201, receive operator inputs from external switches or controls such as foot operated switches or controls, provide, set, or display alerts to a user based on operations of or forces applied to the cutting tool 200, and send and receive signals to and from a pump control 520. The resection control 510 illustrated also includes a resection display panel 518, which may be used to communicate information to a user and may be used to input settings or other information into the resection control 510 or other connected components of the control system.

Other knobs, switches, controls, and the like may be used to control, set, or calibrated the resection control 510 as well.

In the illustrated embodiment, the pump control 520 is configured to manage fluids used during surgery performed with the cutting tool 200. For example and without limitation, fluids such as saline may be used during endoscopic surgical procedures to provide a clear operating medium in which to perform endoscopic surgical tasks. The pump control 520 may be used to one or more of provide fluid to the drive unit 201, sense operating parameters of the drive unit 201, manage waste fluid, receive operator inputs from external switches or controls such as foot operated switches or controls, and send and receive signals to and from the resection control 510. A fluid inflow line 521 is shown coupled between the pump control 520 and a patient joint cannula 522. The patient joint cannula 522 may provide one or both a passageway through which the cutting tool 200 may be introduced into a joint and an entry port for fluid supplied though the fluid inflow line 521. In other embodiments, one or more additional fluid lines may be used to supply fluid or remove fluid from a surgical site from locations different than those illustrated. A saline bag 523 is shown providing a fresh fluid supply to the pump control 520 through a supply line 524 in the present embodiment. A suction line 525 is shown coupled between the cutting tool 200 and the pump control 520, which when activated draws waste fluid through the cutting tool 200 and into the pump control 520 where the fluid may be diverted for waste removal. A waste line 527 is shown coupled between the pump control 520 and a waste receptacle 529. Any other effective supply or waste handling mechanisms may be used in other embodiments. The pump control 520 illustrated also includes a pump control display panel 528, which may be used to communicate information to a user and may be used to input settings or other information into the pump control 520 or other connected components of the control system. Other knobs, switches, controls, and the like may be used to control, set, or calibrated the pump control 520 as well.

Figure 14:
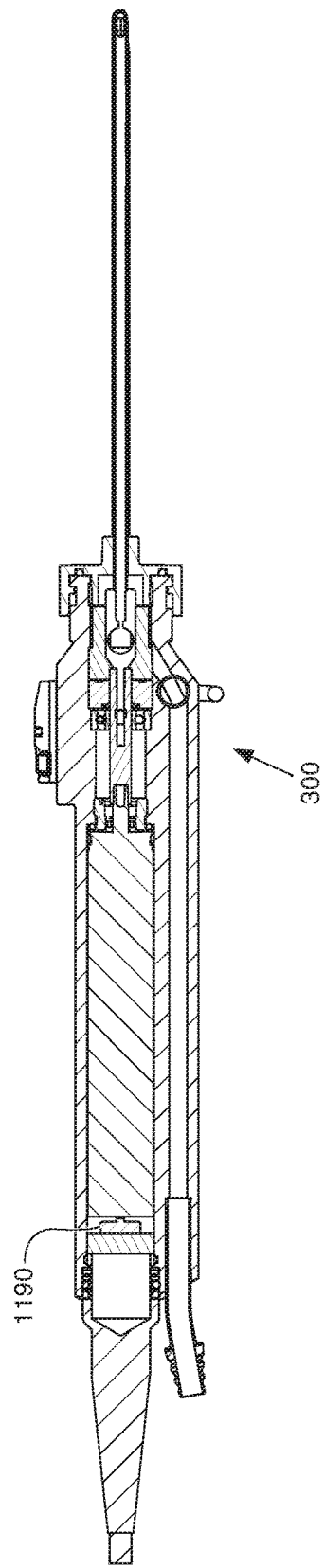
FIG. 14 is a cross-sectional view of an embodiment of a cutting tool.

A cutting tool 300 and its component parts are illustrated in FIG. 14. The cutting tool 300 illustrated is essentially similar to the cutting tool 200, with the addition of the axial sensor 1190. The axial sensor 1190 shown is placed behind the drive unit's motor to register load applied along the longitudinal axis of the cutting tool 300. In other embodiments, an axial sensor could be of any type and could be positioned at any location capable of registering an axial force applied to a working assembly of the cutting tool 300. Function and control of the cutting tool 300 may be otherwise essentially similar to the descriptions provided herein for the cutting tools 100, 200.

Another embodiment of the invention is a method of calibrating a cutting tool that has integrated force sensors. For example and without limitation, any of the cutting tool 100, the cutting tool 200, or the cutting tool 300 could be used in such an embodiment. Method embodiments may include providing a drive unit, a working assembly, and two or more sensors as have been described herein in association with the cutting tools 100, 200, 300. Such a method of calibrating a cutting tool may include applying a limit load to the working assembly. A limit load is a load that a designer or user of a cutting tool does not wish to exceed while the cutting tool is being operated. A limit load may be established empirically or through design calculations. An example of an empirical determination of a limit load may include engaging a skilled operator such as a surgeon to apply a load to an operating cutting tool in an amount beyond which, in the surgeon's judgment, operation of the cutting tool should not be continued. Similarly, a load could be applied to an operating cutting tool until it is judged that the cutting tool should not be operated further to avoid damage to the cutting tool. A load limit may be established through design calculations by, for example, calculating a load based on the characteristics of the cutting tool that would create an unacceptable deflection or unacceptable stress in the cutting tool.

With a limit load applied to a cutting tool, the method of calibrating the cutting tool may further include the act of registering a measured load on one or more of the sensors 190, 290, 1190 that results from application of the limit load. In some embodiments, the act of registering a measured load on one or more sensors includes measuring a load on only one of the sensors and not measuring any significant load on any other sensors. As used herein the term "significant load" means a load that is reasonably measurable in light of the loads that are typically applied to a working assembly. For example, in such an embodiment load may have been applied transversely to the longitudinal axis of the working assembly substantially in radial alignment with the only one of the sensors 190, 290 that measured a load. Consequently, the sensor in a position away from which load is being applied and the sensors with faces transverse to the direction of the applied load would not register a significant load. In other embodiments, the act of registering a measured load may include measuring loads on two or more sensors from which a resultant load is calculated. For example, where a load is applied to a working assembly in a direction between two sensors, some force would be measurable at each of the sensors. Some force may also be measured alone or in combination at an axial sensor such as the axial sensor 1190. A resultant load may be calculated based on the relative magnitudes and directions of the measured loads. Therefore, a measured load to be compared with a limit load may be calculated for a load applied in any particular direction. In still another embodiment, a database of measured loads for all sensors based on applied limit loads may be created by applying a range of limit loads to a cutting instrument and recording a resulting database of measured loads. Such a database of measured loads could be queried as a lookup table in response to operational loadings to determine when limit loads have been reached.

The method of calibrating a cutting tool may further include setting an alert to be activated when the measured load registered on one or more sensors is reached. Various types of alerts may be set. As discussed in describing the system of FIG. 8, an alert may include visual, audio, vibratory, tactile, or any effective alert mechanism. An alert may also take the form of a degraded, reversed, or halted operation of a drive unit. The act of setting an alert to be activated when the measured load registered on one or more sensors is reached may include setting different measured loads to be reached for different types of working assemblies. Different measured loads may be set for working assemblies of different sizes or different types. For example and without limitation, a greater measured load may be set for a blade with a larger diameter or shorter length than would be set for a blade with a relatively smaller diameter or longer length. Drive units of some embodiments may automatically set a measured load at which an alert will respond. This automatic response may be a result of a working assembly being identified to a drive unit. The identifying act may result from user identification of a working assembly or may result from automatic identification by a drive unit. A non-limiting example of automatic identification and automatic setting of a measured load is a system that includes one or more working assemblies with an arrangement or specific placement of magnets readable by a drive unit. Upon reading of the arrangement of magnets, such a drive unit may automatically set a measured load beyond which an alert will be activated. In other embodiments, a drive unit may automatically set a measured load by identifying a working assembly based on any effective identification mechanism. For example and without limitation, identification may result from reading a radio frequency identification (RFID) code, an optical code, or a mechanical characteristic of a working assembly.

Another method embodiment is a method of determining a lateral load on a cutting tool with one or more rotating components. For example and without limitation, any of the cutting tools 100, 200, 300 could be used in such an embodiment. Method embodiments may include providing a drive unit, a working assembly, and two or more sensors as have been described herein in association with the cutting tools 100, 200, 300. The method of determining a lateral load on a cutting tool may include operating the cutting tool and applying a lateral load on the cutting tool. Such a lateral load may be applied to one or more of the working assembly housing, the cutting element, the rotatable shaft, and the cannular shaft. Method embodiments may further include measuring load at the two or more sensors while the cutting tool is being operated. For example and without limitation, sensors 190, 290 of the embodiments disclosed or any other effective arrangement of sensors may be monitored and measured. The method of determining a lateral load is dependent on the direction of the applied load relative to the placement of the sensors. The present method contemplates at least two scenarios. First, if only one sensor measures a significant load, as defined herein, then the method further includes the act of comparing the measured load to a limit load to determine if an alert should be activated. Second, if more than one sensor measures a significant load, then the method further includes the act of calculating a resultant load from the loads measured and comparing the resultant load to the limit load to determine if an alert should be activated.

Various embodiments of a system wholly or its components individually may be made from any biocompatible material. For example and without limitation, biocompatible materials may include in whole or in part: non-reinforced polymers, reinforced polymers, metals, ceramics, adhesives, reinforced adhesives, and combinations of these materials. Reinforcing of polymers may be accomplished with carbon, metal, or glass or any other effective material. Examples of biocompatible polymer materials include polyamide base resins, polyethylene, Ultra High Molecular Weight (UHMW) polyethylene, low density polyethylene, polymethylmethacrylate (PMMA), polyetheretherketone (PEEK), polyetherketoneketone (PEKK), a polymeric hydroxyethylmethacrylate (PHEMA), and polyurethane, any of which may be reinforced. Example biocompatible metals include stainless steel and other steel alloys, cobalt chrome alloys, zirconium, oxidized zirconium, tantalum, titanium, titanium alloys, titanium-nickel alloys such as Nitinol and other superelastic or shape-memory metal alloys.

Terms such as proximal, distal, near, and the like have been used relatively herein. However, such terms are not limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A method of calibrating a cutting tool with integrated force sensors comprising:
    coupling, by releasable locking, a drive unit with a working assembly having a proximal end, a distal end, and a longitudinal axis that passes between the proximal end and the distal end, the working assembly configured to at least in part be rotated by the drive unit, and further wherein the working assembly and drive unit are coupled by alignment of guide pins and notches;
    applying a load to the working assembly, the load defining a limit load;
    measuring, by way of a sensor disposed in the drive unit and adjacent to the proximal end of the working assembly, the limit load applied to the working assembly as a measured load;
    registering the measured load; and
    setting an alert mechanism based on the measured load such that the alert mechanism activates an alert when the sensor measures a load greater than the measured load.

2. The method of claim 1 wherein the limit load is applied at least in part transverse to the longitudinal axis.

3. The method according to claim 1 wherein the limit load is applied in some component part substantially parallel with the longitudinal axis.

4. The method according to claim 1 wherein registering the measured load includes measuring a load on only the sensor and not measuring any significant load on any other sensors.

5. The method according to claim 1 wherein registering the measured load includes measuring loads on two or more sensors from which a resultant load is calculated.

6. The method according to claim 1 wherein setting the alert mechanism includes setting the alert mechanism based on different measured loads to be reached for different types of working assemblies.

7. The method according to claim 1 wherein setting the alert mechanism includes setting one or more of a visual alert, an audio alert, a tactile alert, or an alert that interrupts rotation of a part of the working assembly.

8. The method according to claim 1 further comprising automatically setting, by the drive unit and in response to an identity of the working assembly, a different measured load at which an alert will respond.

9. The method of claim 8 wherein the drive unit automatically sets the different measured load by identifying a working assembly based on an arrangement of magnets in the working assembly.

10. The method of claim 8 wherein the drive unit automatically sets the different measured load by identifying a working assembly based on an RFID tag present in the working assembly.

11. A method of determining a lateral load on a cutting tool with one or more rotating components comprising:
    coupling, by releasable locking, a drive unit to a working assembly having a proximal end, a distal end, and a longitudinal axis that passes between the proximal end and the distal end, the working assembly including a shaft configured to at least in part be rotated by the drive unit, and further wherein the drive unit and working assembly are coupled by alignment of guide pins and notches;

operating the cutting tool and applying a lateral load to the cutting tool;

while the cutting tool is being operated:
- measuring, by a first sensor of two or more sensors, a first significant load, the two or more sensors disposed in the drive unit and spaced around a periphery of the proximal end of the working assembly;
- measuring, by a second sensor of the two or more sensors, a second significant load;

calculating a resultant load from the first and second significant loads; and activating an alert in response to determining the resultant load is greater than the limit load.

* * * * *